(12) United States Patent
Xu et al.

(10) Patent No.: US 8,968,523 B2
(45) Date of Patent: *Mar. 3, 2015

(54) RECOVERY OF BUTANOL ISOMERS FROM A MIXTURE OF BUTANOL ISOMERS, WATER, AND AN ORGANIC EXTRACTANT

(75) Inventors: Yihui Tom Xu, Newark, DE (US); William D. Parten, Wilmington, DE (US)

(73) Assignee: Butamax Advanced Biofuels LLC, Wilmington, DE (US)

( * ) Notice: Subject to any disclaimer, the term of this patent is extended or adjusted under 35 U.S.C. 154(b) by 261 days.

This patent is subject to a terminal disclaimer.

(21) Appl. No.: 12/834,916

(22) Filed: Jul. 13, 2010

(65) Prior Publication Data

US 2011/0162954 A1    Jul. 7, 2011

Related U.S. Application Data

(60) Provisional application No. 61/225,662, filed on Jul. 15, 2009.

(51) Int. Cl.
*B01D 3/40* (2006.01)
*C07C 29/84* (2006.01)
(Continued)

(52) U.S. Cl.
CPC ............... *B01D 3/002* (2013.01); *B01D 3/143* (2013.01); *C07C 29/84* (2013.01)
USPC ............. 203/50; 203/51; 203/60; 203/61; 203/62; 203/63; 203/78; 203/79; 203/18; 203/57; 568/913; 568/916

(58) Field of Classification Search
USPC ........... 203/14, 18, 50, 51, 57, 60, 61, 62, 63, 203/78, 80; 568/913, 916, 918
See application file for complete search history.

(56) References Cited

U.S. PATENT DOCUMENTS 4,428,798 A * 1/1984 Zudkevitch et al. ............ 203/18
4,511,437 A * 4/1985 Heck et al. ...................... 203/19
(Continued)

FOREIGN PATENT DOCUMENTS

WO         2008143704      11/2008
WO     WO 2009/013160      1/2009

OTHER PUBLICATIONS

Vane, "Separation technologies for the recovery and dehydration of alcohols from fermentation broths", Biofuels, Bioproducts & Biorefining, John Wiley & Sons, Ltd., GB, vol. 2, No. 6, Nov. 1, 2008, pp. 553-588.
(Continued)

*Primary Examiner* — Virginia Manoharan

(57) ABSTRACT

A process for recovering butanol from a mixture of a water-immiscible organic extractant, water, butanol, and optionally a non-condensable gas, is provided. The butanol is selected from 1-butanol, isobutanol, and mixtures thereof. An overhead stream from a first distillation column is decanted into two liquid phases. The wet butanol phase is refined in a second distillation column; the aqueous phase is returned to the first distillation column. A portion of the wet butanol phase from the decanter is also returned to the first distillation column. The extractant may be $C_7$ to $C_{22}$ fatty alcohols, $C_7$ to $C_{22}$ fatty acids, esters of $C_7$ to $C_{22}$ fatty acids, $C_7$ to $C_{22}$ fatty aldehydes, and mixtures thereof.

14 Claims, 2 Drawing Sheets

(51) Int. Cl.
*C07C 29/86* (2006.01)
*C07C 31/12* (2006.01)
*B01D 3/00* (2006.01)
*B01D 3/14* (2006.01)

(56) References Cited

U.S. PATENT DOCUMENTS

| | | | |
|---|---|---|---|
| 4,636,284 A * | 1/1987 | English et al. | 203/18 |
| 4,784,868 A * | 11/1988 | Young | 426/493 |
| 4,865,973 A | 9/1989 | Kollerup et al. | |
| 4,978,430 A * | 12/1990 | Nakagawa et al. | 203/14 |
| 5,985,100 A * | 11/1999 | Aron et al. | 203/74 |
| 7,128,814 B2 * | 10/2006 | Beckmann et al. | 203/2 |
| 7,311,813 B2 | 12/2007 | Reyneke et al. | |
| 2007/0092957 A1 | 4/2007 | Donaldson et al. | |
| 2008/0132741 A1 * | 6/2008 | D'Amore et al. | 568/840 |
| 2009/0030537 A1 | 1/2009 | Hartle | |
| 2009/0305370 A1 | 12/2009 | Grady et al. | |
| 2010/0221802 A1 | 9/2010 | Grady et al. | |
| 2011/0097773 A1 | 4/2011 | Grady et al. | |

OTHER PUBLICATIONS

Oudshoorn et al., "Assessment of options for selective 1-butanol recovery from aqueous solution", Industrial & Engineering Chemistry Research, vol. 48, Jun. 24, 2009, pp. 7325-7336.

Ezeji et al., "Bioproduction of butanol from biomass: from genes to bioreactors", Current Opinion in Biotechnology, London, GB, vol. 18, No. 3, Jun. 8, 2007, pp. 220-227.

Griffith et al., "1-butanol extraction with vegetable-oil fatty-acid esters", Jan. 1, 1983, Developments in Industrial Microbiology, Elsevier Science BV, Amsterdam, NL, pp. 795-800.

U.S. Appl. No. 12/758,870, filed Apr. 13, 2010.

International Search Report and Written Opinion in corresponding PCT/US2010/042095.

Groot, et al., Technologies for Butanol Recovery Integrated with Fermentations, Process Biochem. 27:61-75, 1992.

Roffler, et al., In situ Extractive Fermentation of Acetone and Butanol, Bitechnol. Bioeng, 31:135-143, 1988.

Roffler, et al., Extractive Fermentation of Acetone and Butanol: Process Design and Economic Evaluation, Biotechnol, Process 3:131-140, 1987.

Schugerl, Integrated Processing of Biotechnology Products, Biotechnol. Adv. 18:581-599, 2000.

Shi, et al., Performance Evaluation of Acetone-Butanol Continuous Flash Extractive Fermentation Process, Bioprocess Biosyst. Eng. 27:175-183, 2005.

Roffler, et al., In-situ recovery of butanol during fermentation, Part 1: Batch extractive fermentation, Bioprocess Engineer, 2:1-12, 1987.

Evans, et al., Enhancement of Butanol Formation by Clostridium acetobutylicum in the Presence of Decanol-Oleyl Alcohol Mixed Extractants, Appl. Environ. Microbiol. 54:1662-1667, 1988.

* cited by examiner

RECOVERY OF BUTANOL ISOMERS FROM A MIXTURE OF BUTANOL ISOMERS, WATER, AND AN ORGANIC EXTRACTANT

CROSS REFERENCE TO RELATED APPLICATIONS

This application claims the benefit of priority to U.S. Provisional Patent Application 61/225,662, filed Jul. 15, 2009, the entirety of which is herein incorporated by reference.

FIELD OF THE INVENTION

Processes for recovering butanol from a butanol-containing organic phase obtained from an extractive fermentation process are provided. Specifically, processes for separating butanol from a mixture comprising butanol, water, a water-immiscible organic extractant, and optionally a non-condensable gas, are provided.

BACKGROUND OF THE INVENTION

Butanol is an important industrial chemical with a variety of applications, such as use as a fuel additive, as a blend component to diesel fuel, as a feedstock chemical in the plastics industry, and as a foodgrade extractant in the food and flavor industry. Each year 10 to 12 billion pounds of butanol are produced by petrochemical means. As the projected demand for butanol increases, interest in producing butanol from renewable resources such as corn, sugar cane, or cellulosic feeds by fermentation is expanding.

In a fermentative process to produce butanol, in situ product removal advantageously reduces butanol inhibition of the microorganism and improves fermentation rates by controlling butanol concentrations in the fermentation broth. Technologies for in situ product removal include stripping, adsorption, pervaporation, membrane solvent extraction, and liquid-liquid extraction. In liquid-liquid extraction, an extractant is contacted with the fermentation broth to partition the butanol between the fermentation broth and the extractant phase. The butanol and the extractant are recovered by a separation process, for example by distillation. In the recovery process, the butanol can also be separated from any water, non-condensable gas, and/or fermentation by-products which may have been removed from the fermentation broth through use of the extractant.

Processes for recovering butanol from the butanol-containing extractant phase obtained by in situ product removal from a fermentation broth are sought. Economical processes for recovering butanol substantially free of water and of the extractant are desired. Also desired are separation processes which minimize degradation of the extractant.

SUMMARY OF THE INVENTION

The present invention provides a process for separating a butanol selected from the group consisting of 1-butanol, isobutanol, and mixtures thereof, from a feed comprising a water-immiscible organic extractant, water, the butanol, and optionally a non-condensable gas.

In one aspect, the present invention is a process comprising the steps:
a) introducing a feed comprising:
   (i) a water-immiscible organic extractant,
   (ii) water,
   (iii) at least one isomer of butanol, and
   (iv) optionally a non-condensable gas into a first distillation column, wherein the first distillation column comprises a stripping section and optionally a rectifying section at an introduction point above the stripping section, the first distillation column having an operating temperature, $T_1$ and an operating pressure $P_1$ at a predetermined point in the stripping section, wherein $T_1$ and $P_1$ are selected to produce a first bottoms stream and a first vaporous overhead stream, the first bottoms stream comprising the water-immiscible organic extractant and water and being substantially free of butanol, and the first vaporous overhead stream comprising water, butanol, and the optional non-condensable gas;

b) condensing the first vaporous overhead stream to produce a gas phase and recover a first mixed condensate, wherein the first mixed condensate comprises
   (i) a butanol phase comprising butanol, less than about 30 wt % water; and
   (ii) an aqueous phase comprising water and less than about 10 wt % of butanol;

c) introducing at least a portion of the aqueous phase to the first distillation column;

d) introducing a first portion of the butanol phase into a second distillation column having at least a stripping section; and e) operating the second distillation column to produce a second bottoms stream comprising butanol and being substantially free of water, and a second vaporous overhead stream comprising butanol and water;

wherein the extractant is selected such that it (A) preferentially dissolves butanol over water and (B) is separable from butanol by distillation.

DETAILED DESCRIPTION OF THE INVENTION

Figure 1:
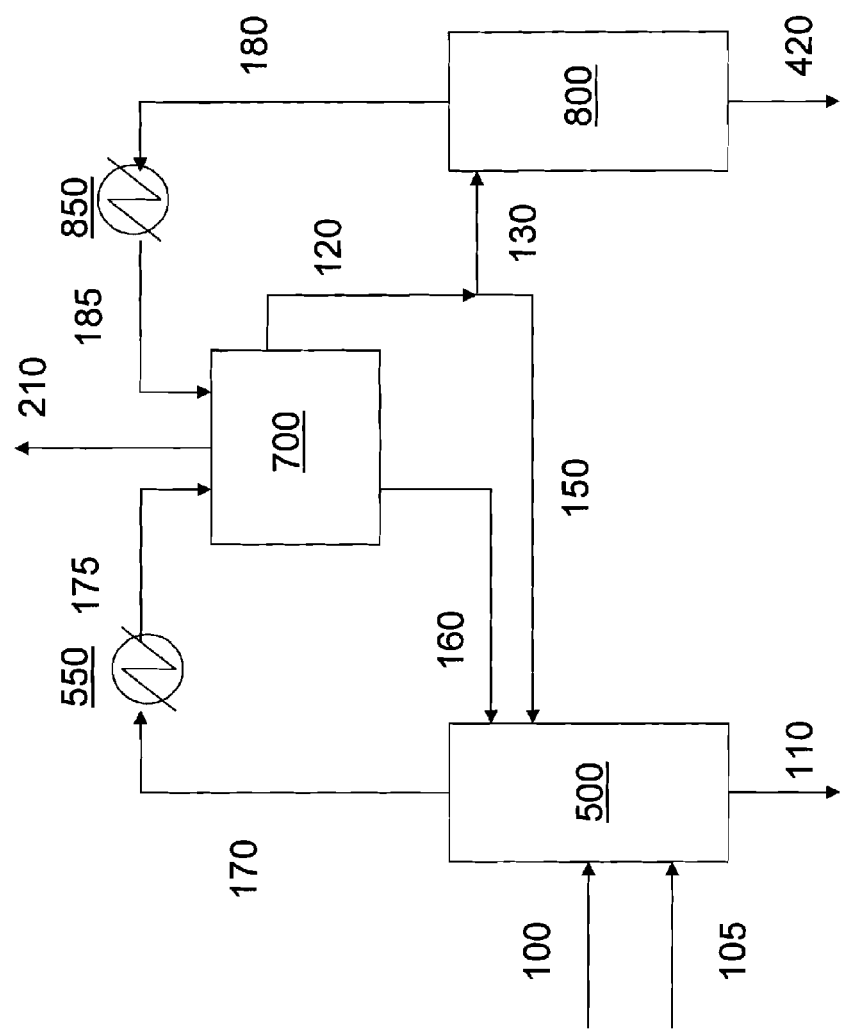
FIG. 1 illustrates one embodiment of a system useful for practicing the process of the invention.

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

DEFINITIONS

The following definitions are used in this disclosure:

"Butanol" as used herein refers with specificity to the butanol isomers 1-butanol (1-BuOH) and/or isobutanol (iBuOH or I-BUOH), either individually or as mixtures thereof. 2-Butanol and tert-butanol (1,1-dimethyl ethanol) are specifically excluded from the present invention.

"In Situ Product Removal" as used herein means the selective removal of a specific fermentation product from a biological process such as fermentation to control the product concentration in the biological process.

"Fermentation broth" as used herein means the mixture of water, sugars, dissolved solids, suspended solids, microorganisms producing butanol, product butanol and all other constituents of the material held in the fermentation vessel in which product butanol is being made by the reaction of sugars to butanol, water and carbon dioxide ($CO_2$) by the microorganisms present. The fermentation broth is the aqueous phase in biphasic fermentative extraction. From time to time, as used herein the term "fermentation medium" may be used synonymously with "fermentation broth".

"Fermentation vessel" as used herein means the vessel in which the fermentation reaction by which product butanol is made from sugars is carried out. The term "fermentor" may be used synonymously herein with "fermentation vessel".

The term "effective titer" as used herein, refers to the total amount of butanol produced by fermentation per liter of fermentation medium. The total amount of butanol includes: (i) the amount of butanol in the fermentation medium; (ii) the amount of butanol recovered from the organic extractant; and (iii) the amount of butanol recovered from the gas phase, if gas stripping is used.

The term "aqueous phase titer" as used herein, refers to the concentration of butanol in the fermentation broth.

"Stripping" as used herein means the action of transferring all or part of a volatile component from a liquid stream into a gaseous stream.

"Stripping section" as used herein means that part of the contacting device in which the stripping operation takes place.

"Rectifying" as used herein means the action of transferring all or part of a condensable component from a gaseous stream into a liquid stream in order to separate and purify lower boiling point components from higher boiling point components.

"Rectifying section" as used herein means the section of the distillation column above the feed point, i.e. the trays or packing material located above the point in the column where the feed stream enters, where the rectifying operation takes place.

The term "separation" as used herein is synonymous with "recovery" and refers to removing a chemical compound from an initial mixture to obtain the compound in greater purity or at a higher concentration than the purity or concentration of the compound in the initial mixture.

The term "water-immiscible" refers to a chemical component, such as an extractant or solvent, which is incapable of mixing with an aqueous solution, such as a fermentation broth, in such a manner as to form one liquid phase.

The term "extractant" as used herein refers to one or more organic solvents which are used to extract butanol from a fermentation broth.

The term "organic phase", as used herein, refers to the non-aqueous phase of a biphasic mixture obtained by contacting a fermentation broth with a water-immiscible organic extractant.

The term "fatty acid" as used herein refers to a carboxylic acid having a long, aliphatic chain of $C_7$ to $C_{22}$ carbon atoms, which is either saturated or unsaturated.

The term "fatty alcohol" as used herein refers to an alcohol having a long, aliphatic chain of $C_7$ to $C_{22}$ carbon atoms, which is either saturated or unsaturated.

The term "fatty aldehyde" as used herein refers to an aldehyde having a long, aliphatic chain of $C_7$ to $C_{22}$ carbon atoms, which is either saturated or unsaturated.

Non-condensable gas means a gas that is not condensed at an operating temperature of the process described herein.

Butanol-containing extractant streams useful as a feed in the processes of this invention include any organic phase obtained from an extractive fermentation wherein butanol is produced as a fermentation product. Typical butanol-containing extractant streams include those produced in "dry grind" or "wet mill" fermentation processes in which in situ product removal is practiced using liquid-liquid extraction of the fermentation broth with an organic extractant. After extraction, the extractant stream typically comprises butanol, water, and the extractant. The extractant stream may optionally comprise a non-condensable gas, which can be a gas that is inert or otherwise non-reactive with other feed components under the operating conditions of the present invention. Such gases can be selected from gases in the group consisting of, for example, carbon dioxide, nitrogen, hydrogen, Noble gases such as argon, or mixtures of any of these. The extractant stream may optionally further comprise fermentation by-products having sufficient solubility to partition into the extractant phase. Butanol-containing extractant streams useful as a feed in the processes of the invention include streams characterized by a butanol concentration in the feed from about 0.1 weight percent to about 40 weight percent, for example from about 2 weight percent to about 40 weight percent, for example from about 5 weight percent to about 35 weight percent, based on the weight of the feed. Depending on the efficiency of the extraction, the aqueous phase titer of butanol in the fermentation broth can be, for example, from about 5 g/L to about 85 g/L, or from about 10 g/L to about 40 g/L.

The extractant is a water-immiscible organic solvent or solvent mixture having characteristics which render it useful for the extraction of butanol from a fermentation broth. The extractant preferentially partitions butanol from the aqueous phase, for example by at least a 1.1:1 concentration ratio, such that the concentration of butanol in the extractant phase is at least 1.1 times that in the aqueous phase when evaluated in a room-temperature extraction of an aqueous solution of butanol. Preferably, the extractant preferentially partitions butanol from the aqueous phase by at least a 2:1 concentration ratio, such that the concentration of butanol in the extractant phase is at least two times that in the aqueous phase when evaluated in a room-temperature extraction of an aqueous solution of butanol.

To be of practical use in the butanol recovery process, the extractant is separable from butanol by distillation, having a boiling point at atmospheric pressure which is at least about 30 degrees Celsius higher than that of the butanol to be recovered, or for example at least about 40 degrees higher, or for example at least about 50 degrees higher.

The extractant comprises at least one solvent selected from the group consisting of $C_7$ to $C_{22}$ fatty alcohols, $C_7$ to $C_{22}$ fatty acids, esters of $C_7$ to $C_{22}$ fatty acids, $C_7$ to $C_{22}$ fatty aldehydes, $C_7$ to $C_{22}$ fatty amides and mixtures thereof. Suitable organic extractants are further selected from the group consisting of oleyl alcohol (CAS No. 143-28-2), behenyl alcohol (CAS No. 661-19-8), cetyl alcohol (CAS No. 36653-82-4), lauryl alcohol, also referred to as 1-dodecanol (CAS No. 112-53-8), myristyl alcohol (112-72-1), stearyl alcohol (CAS No. 112-92-5), 1-undecanol (CAS No. 112-42-5), oleic acid (CAS No. 112-80-1), lauric acid (CAS No. 143-07-7), myristic acid (CAS No. 544-63-8), stearic acid (CAS No. 57-11-4), methyl myristate CAS No. 124-10-7), methyl oleate (CAS No. 112-62-9), undecanal (CAS No. 112-44-7), lauric aldehyde (CAS No. 112-54-9), 2-methylundecanal (CAS No. 110-41-8), oleamide (CAS No. 301-02-0), linoleamide (CAS No. 3999-

01-7), palmitamide (CAS No. 629-54-9) and stearylamide (CAS No. 124-26-5) and mixtures thereof. In some aspects, the extractant comprises oleyl alcohol. Suitable solvents are described in U.S. Patent Application Publication No. 2009030537 and also in U.S. application Ser. Nos. 12/759,283 and 12/758,870 (both filed Apr. 13, 2010), all of which are incorporated herein by reference.

These organic extractants are available commercially from various sources, such as Sigma-Aldrich (St. Louis, Mo.), in various grades, many of which may be suitable for use in extractive fermentation to produce or recover butanol. Technical grades contain a mixture of compounds, including the desired component and higher and lower fatty components. For example, one commercially available technical grade oleyl alcohol contains about 65% oleyl alcohol and a mixture of higher and lower fatty alcohols.

The invention provides processes for separating or recovering butanol from a feed comprising a water-immiscible organic extractant, water, the butanol, and optionally a non-condensable gas. Separation of the butanol from the feed is achieved through a combination of distillation and decantation. The distillation involves the use of at least two distillation columns. The first column, in combination with decantation, effects a separation of any non-condensable gas, such as carbon dioxide, and butanol from the extractant, for example oleyl alcohol, and water. The cooled overhead stream from the first column is decanted into two liquid phases. At least a portion of the aqueous phase from the decanter is returned to the first column; a portion of the organic phase is also returned to the first column. The second column effects a separation of butanol and water and provides a butanol bottoms stream which is substantially free of water. By "substantially free of water" it is meant that less than about 0.01 wt % of water is present bottoms stream.

The processes of the invention can be understood by reference to FIG. 1, which illustrates one embodiment of a system useful for practicing the process of the invention. The feed stream 100, obtained from a fermentation vessel (not shown) or an extractor (not shown) in a process for fermentative extraction, is introduced into a first distillation column 500, which has a stripping section and optionally a rectifying section, at a feed point above the stripping section. The feed stream 100 is distilled to provide a first bottoms stream 110 and a first vaporous overhead stream 170 comprising water, butanol, and any non-condensable gas if present in the feed. An operating temperature $T_1$ and an operating pressure $P_1$ at a predetermined point in the stripping section of column 500 are selected so as to provide the first bottoms stream 110 comprising the extractant and water and being substantially free of butanol. By "substantially free of butanol" it is meant that butanol comprises no more than 0.01 wt % of the bottoms 110. The distillation column 500 can be any conventional column having at least a feed inlet, an overhead vapor outlet, a bottoms stream outlet, a heating means, and a sufficient number of stages to effect the separation of the butanol from the extractant. A rectification section is required when minimum oleyl alcohol loss in stream 130 is desired and may or may not be combined with use of an organic reflux stream 150. In the case where the extractant comprises oleyl alcohol, distillation column 500 should have at least 5 stages including a re-boiler.

The first bottoms stream 110 can include from about 3 to about 12 weight percent water, and less than about 0.01 weight percent butanol. To ensure that the bottom stream 110 is substantially free of butanol, the ratio of the aqueous to organic reflux flows to distillation column 500 should be chosen such that the aqueous reflux (stream 160) exceeds the organic reflux (stream 150) by a ratio higher than the ratio of water to the organic composition of the azeotrope. The process may further comprise introducing bottoms stream 110 from the first distillation column into a fermentation vessel (not shown). Alternatively, bottoms stream 110 may be separated (not shown) to obtain a bottoms aqueous phase comprising water and a bottoms organic phase comprising the extractant, introducing at least a portion of the bottoms organic phase into a fermentation vessel, and optionally introducing at least a portion of the bottoms aqueous phase into the same or a different fermentation vessel. The separation may be done, for example, by cooling the bottoms stream 110 until phase separation occurs. These options provide means to recycle the first bottoms stream 110 from the butanol recovery process to the extractive fermentation process.

Optionally, additional stream 105 comprising water, steam, or a mixture thereof may be introduced into the first distillation column 500 at a point anywhere along the column. If water is used, it is preferred that the water be fed together with aqueous stream 160, which is returned as liquid reflux. If steam is used, it is preferred that the steam be fed in the stripping section or from the bottom of the column. The feed point of stream 105 may be the same as or different from the feed point of feed stream 100. The total aqueous return to the column is the sum of the aqueous stream 160 and the optional stream 105, and the total aqueous return to the column should be chosen so as to be sufficient to maintain liquid water throughout all the column trays. The amount of any added water, steam, or a mixture thereof should also be chosen such that, in combination with aqueous stream 160, the total aqueous return to the column exceeds the butanol stream 150 returned to the column by a ratio that is greater than the ratio of the aqueous composition to the organic composition of the azeotrope.

The vaporous overhead stream 170 from the first distillation column can include up to about 65.6 weight percent butanol and at minimum about 32.5 weight percent water. The overhead stream includes non-condensable gas that may have been present in the feed. Stream 170 is condensed in a condenser 550 to produce a first mixed condensate stream 175 comprising condensed liquid butanol and condensed liquid water. Stream 175 also includes any non-condensable gas present in the feed. The condenser 550 may be of any conventional design.

The mixed condensate stream 175 is introduced into a decanter 700 and allowed to separate into a liquid butanol phase and a liquid aqueous phase. The temperature of the decanter is preferably maintained at or below about 40° C. to reduce the amount of butanol and water being stripped out by the non-condensable gas. The liquid butanol phase, the lighter liquid phase (the top liquid phase), can include less than about 30 wt %, or from about 16 to about 30 weight percent, water and may further comprise less than about 0.001 weight percent of residual extractant which comes overhead in column 500. The fraction of extractant in the butanol phase can be minimized by use of a rectification section in column 500. The liquid aqueous phase includes less than about 10 wt %, or from about 3 to about 10 weight percent butanol. The decanter may be of any conventional design.

When a non-condensable gas such as carbon dioxide is present in the feed, the non-condensable gas is present in stream 170 and in stream 175. At least a portion of the gas phase comprising the non-condensable gas can be purged from the process, as shown in FIG. 1, in which purge stream 210 comprising the non-condensable gas is shown leaving the decanter 700.

From the decanter 700, at least a portion of the aqueous phase 160 is introduced to the first distillation column 500. The aqueous phase 160 may be introduced as reflux to the column and will typically include all of the aqueous phase separated in the decanter. Introducing stream 160 into column 500 lowers the column temperature and ensures that water is present in the bottoms stream. This is advantageous because higher column temperatures can result in degradation of the extractant in the column bottoms, particularly in the case where fermentation byproducts such as organic acids are present and the extractant contains functional groups, such as unsaturated carbon-carbon bonds in the case of oleyl alcohol. Degradation of the extractant should be avoided as it can cause decreased efficiency in the extractive fermentation process.

The process may optionally further comprise introducing at least a portion of the aqueous phase from the decanter into a fermentation vessel (not shown). This can provide a means to recycle some of the water from the butanol recovery process back to the extractive fermentation process. However, it is normally preferred to recycle water to the fermenter via stream 110, in which the butanol content is lower.

The butanol phase 120 leaving the decanter is split into two portions. A first portion of the butanol phase, stream 130, is introduced into a second distillation column 800, which has a stripping section, at a feed point above the stripping section. The stream 130 is distilled to provide a second bottoms stream 420 comprising butanol and a second vaporous overhead stream 180 comprising butanol and water. The second distillation column is operated so as to provide the bottoms stream 420 substantially free of water. By "substantially free of water" it is meant that the bottoms 420 include less than about 0.01 weight percent water. The distillation column 800 can be any conventional column having at least a feed inlet, an overhead vapor outlet, a bottoms stream outlet, a heating means, a stripping section, and a sufficient number of stages to effect the desired separation. Column 800 should have at least 6 stages a including re-boiler.

A second portion of the butanol phase, stream 150, is introduced into the first distillation column 500. Stream 150 may be introduced as reflux to the column. Introducing stream 150 into column 500 as reflux will suppress extractant loss in vaporous stream 170 of column 500. The ratio of stream 150 over stream 120 can range from 0.1 to 50 weight percent.

The vaporous overhead stream 180 from the second distillation column 800 includes about 66.5 weight percent butanol and about 32.5 weight percent water. Stream 180 is condensed in a condenser 850 to produce a second condensate stream 185 comprising butanol and water. The condenser 850 may be of any conventional design. At least a portion of the second condensate stream 185 may be introduced into the first mixed condensate stream, for example by feeding the second condensate steam 185 into decanter 700. The combined first mixed condensate stream and second condensate stream are then allowed to separate into a liquid butanol phase and a liquid aqueous phase, and non-condensable gas can be purged as previously described hereinabove.

The vaporous overhead stream 180 may further comprise volatile fermentation byproducts such as acetaldehyde. Optionally, at least a portion of stream 180 may be purged from the process (not shown) to remove volatile fermentation byproducts from the butanol recovery process.

A mixture of higher boiling extractants is expected to behave in a fundamentally similar way to a single extractant provided that the boiling point of the mixture, or the boiling point of the lowest boiling solvent of the mixture, is significantly higher than the boiling points of water and butanol, for example at least about 30 degrees higher.

The present processes for separating or recovering butanol provide butanol known to have an energy content similar to that of gasoline and which can be blended with any fossil fuel. Butanol is favored as a fuel or fuel additive as it yields only $CO_2$ and little or no $SO_x$ or $NO_x$ when burned in the standard internal combustion engine. Additionally, butanol is less corrosive than ethanol, the most preferred fuel additive to date.

In addition to its utility as a biofuel or fuel additive, the butanol recovered according to the present processes has the potential of impacting hydrogen distribution problems in the emerging fuel cell industry. Fuel cells today are plagued by safety concerns associated with hydrogen transport and distribution. Butanol can be easily reformed for its hydrogen content and can be distributed through existing gas stations in the purity required for either fuel cells or vehicles. Furthermore, the present processes recover butanol obtained from plant derived carbon sources, avoiding the negative environmental impact associated with standard petrochemical processes for butanol production.

One advantage of the present processes for separation or recovery of butanol is that by returning a portion of the aqueous phase from the decanter to the first column, the temperature in the first column is kept relatively low, for example below about 140° C. under any conditions, and in the case of operation at atmospheric pressure, closer to 100° C. Lower temperatures avoid or reduce fouling of the heat exchangers associated with the column, as can occur when the extractant in the bottoms stream degrades, for example through reactions with or catalyzed by fermentation byproducts contained in the bottoms stream. Lower column temperatures also make the recovery process more economical.

An additional advantage is that the first bottoms stream comprising the extractant is substantially free of the butanol product, which contributes to high yield in the recovery process. Being substantially free of butanol also enables optional recycling of the first bottoms stream to the fermentative process. It also simplifies its disposition, should it not be recycled.

Although particular embodiments of the present invention have been described in the foregoing description, it will be understood by those skilled in the art that the invention is capable of numerous modifications, substitutions, and rearrangements without departing from the spirit of essential attributes of the invention. Reference should be made to the appended claims, rather than to the foregoing specification, as indicating the scope of the invention.

The process of the invention can be demonstrated using a computational model of the process. Process modeling is an established methodology used by engineers to simulate complex chemical processes. Process modeling software performs many fundamental engineering calculations, for example mass and energy balances, vapor/liquid equilibrium and reaction rate computations. The modeling of distillation columns is particularity well established. Calculations based on experimentally determined binary vapor/liquid equilibrium and liquid/liquid equilibrium data can predict reliably the behavior of multi-component mixtures. This capability has been expanded to allow modeling of complex multi-stage, multi-component distillation columns using rigorous algorithms like the "inside-out" algorithm developed by Joseph Boston of Aspentech, Inc. of Burlington, Mass. Commercial modeling software, such as Aspen Plus® from Aspentech, can be used in conjunction with physical property databases, such as DIPPR, available from the American Institute of Chemical Engineers, Inc., of New York, N.Y., to develop accurate models and assessments of processes.

EXAMPLES

The Examples were obtained through process modeling using isobutanol as the butanol isomer and oleyl alcohol as the extractant. Similar results would be expected for the analogous cases where 1-butanol or a mixture of 1-butanol and isobutanol was selected as the butanol isomer, due to the similarity of the physical property data for isobutanol and 1-butanol and the heterogeneous nature of the azeotrope between water and these butanol isomers.

Table 1 lists typical feed compositions of the rich solvent stream, obtained from extractive fermentation, entering the isobutanol product recovery area. These compositions were used in modeling the processes of the invention. In the Examples, the term "rich solvent stream" is synonymous with the term "feed stream" used above.

TABLE 1

Feed Compositions (in Weight Percent) of the Rich Solvent Stream from the Extractor

| Feed Compositions | Example 1 | Example 2 |
|---|---|---|
| Isobutanol | 11.44% | 25.1% |
| Water | 6.48% | 8.23% |
| Carbon dioxide | 0.89% | 0.94% |
| Oleyl alcohol | 81.19% | 65.72% |

These composition values for the rich solvent stream were established by a simulation of a dry grind facility using extractive in situ product removal technology producing 50 MM gal/year of isobutanol, and fermenter broth aqueous phase titers of 20 and 40 g/L respectively. It was assumed that the rich solvent stream was at equilibrium with the fermentation broth and that the solvent flow rate was sufficient to meet the specified annual capacity.

Figure 2:
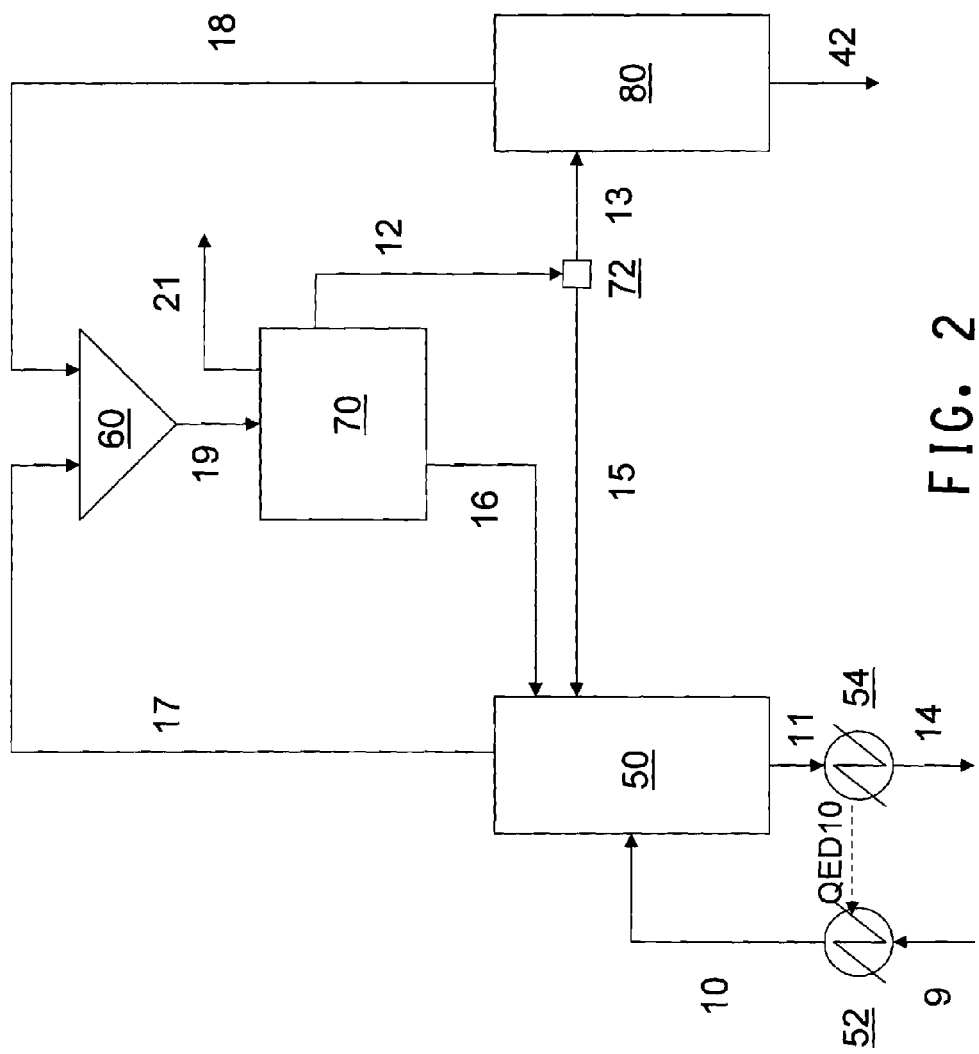
FIG. 2 illustrates a process schematic diagram used in modeling the process of the invention.

The parameters inputted for the simulations of the embodiments of the processes of the invention are listed in Table 2 and follow a process schematic diagram as shown in FIG. 2. In FIG. 2, "QED10" refers to a heat stream representing process to process heat exchange between the solvent column feed and bottom product via heat exchangers 52 and 54. Block 60 represents a mixer combining the two overhead streams 17 and 18. Certain dimensions and duty results calculated from the process model are also listed in Table 2. These parameters do not include physical property parameters, and those related to convergence and other computational options or diagnostics. The organic reflux to the solvent column is expressed in terms of the split fraction on the total flow of the organic phase 12 from the decanter.

TABLE 2

Conditions Used for Modeling Processes of the Invention

| Equipment blocks | Inputs | Example 1 | Example 2 | Units |
|---|---|---|---|---|
| Solvent Column (50) | Number of theoretical stages including re-boiler | 15 | 15 | stages |
| | Column top pressure | 1 | 1 | bar |
| | Column bottom pressure | 1.1 | 1.1 | bar |
| | Column internal diameter | 3.40 | 2.82 | m |
| | Column re-boiler duty | 71639 | 55155 | MJ/hr |
| | Preheated rich solvent feed (10) location | 3 | 3 | stage |
| | Aqueous reflux from decanter (16) location | 1 | 1 | stage |
| | Organic reflux from decanter (15) location | 1 | 1 | stage |
| | Mass fraction isobutanol in bottom lean solvent (11) | 100 | 100 | ppm |
| | Reflux stream temperature | 40 | 40 | deg C. |
| | Preheated rich solvent stream (10) flow rate | 157778 | 71097 | kg/hr |
| | Preheated rich solvent stream (10) temperature | 80.7 | 73.2 | deg C. |
| BUOHCOL Column (80) | Number of theoretical stages including re-boiler | 10 | 10 | stages |
| | Column top pressure | 1 | 1 | bar |
| | Column bottom pressure | 1.05 | 1.05 | bar |
| | Column internal diameter | 2.77 | 2.75 | m |
| | Column re-boiler duty | 33685 | 33369 | MJ/hr |
| | Organic feed from decanter (13) location | 1 | 1 | stage |
| | Organic feed from decanter (13) temperature | 40 | 40 | deg C. |
| | Water mass fraction in bottom product (42) | 100 | 100 | ppm |
| Decanter (70) | Decanter pressure | 1 | 1 | atm |
| | Decanter temperature | 40 | 40 | deg C. |
| | Combined condenser duty of the two columns | −97771 | −83114 | MJ/hr |
| Orsplit (72) | Ratio of stream (15) to all organic from decanter (12) | 0.2 | 0.2 | |

Two cases were run to demonstrate the operating requirements of the processes of the invention. For each case, a particular modification was made to the rich solvent feed flow and compositions from the extractive fermentation process where two different aqueous phase titers were maintained. In each of the independent simulations, column traffic and heat exchanger duties will change because of the feed composition change. By comparing the resulting capital investment and operating costs between different cases, the impact of the rich solvent feed flow and composition on product recovery area performance was quantified. These two examples, however, should not be regarded as process operating limits of this invention.

The term "Solvent Column" is synonymous with the term "first distillation column" used above. The term "BUOHCOL" is synonymous with the term "second distillation column" used above. The abbreviation "OLEYLOH" refers to oleyl alcohol.

Stream results for Example 1 are listed in Table 3. BUOHCOL column traffic and liquid mass composition profiles are listed in Table 4. Solvent column traffic and liquid mass composition profiles are listed in Table 5.

Stream results for Example 2 are listed in Table 6. BUO-HCOL column traffic and liquid mass composition profiles are listed in Table 7. Solvent column traffic and liquid mass composition profiles are listed in Table 8.

Other key process parameters include the following: 1) the total number of theoretical stages in the solvent column and the feed location of the preheated rich solvent stream; 2) the split fraction of organic reflux to solvent column; and 3) the degree of preheating of the rich solvent stream before feeding it to the solvent column. These parameters can be manipulated to achieve optimum separation performance.

Example 1

In this Example, 157,778 kg/hr rich solvent feed (9) containing 11.44 weight percent isobutanol is heated from 32.2° C. to 80.6° C. by a process to process heat exchanger and the resulting stream (10) is fed to the solvent column at stage 3. This feed point divides the solvent column into the rectifying and stripping sections. This rich solvent feed condition corresponds to 20 g/L aqueous phase titer in the fermentor which is maintained during the extractive fermentation process. The separation is realized by a larger diameter solvent column, and higher solvent column re-boiler and condenser duties. Stream (11) contains 92.6 weight percent oleyl alcohol and 7.4 weight percent water. Stream (42) is 99.96 weight percent isobutanol.

Example 2

In this Example, 71,097 kg/hr rich solvent feed (9) containing 25.1 weight percent isobutanol is heated from 32.2° C. to 73.2° C. by a process to process heat exchanger and the resulting stream (10) is fed to the solvent column at stage 3. This feed point divides the solvent column into the rectifying and stripping sections. This rich solvent feed condition corresponds to 40 g/L aqueous phase titer in the fermentor which is maintained during the extractive fermentation process. The separation is realized by a smaller diameter solvent column, and lower solvent column re-boiler and condenser duties. Stream (11) contains 88.9 weight percent oleyl alcohol and 11.1 weight percent water. Stream (42) is 99.99 weight percent isobutanol.

TABLE 3

Simulated Stream Outputs for Example 1.

|  | 9 | 10 | 11 | 12 | 13 | 14 | 15 |
|---|---|---|---|---|---|---|---|
| Temperature C. | 32.2 | 80.6 | 102.3 | 40 | 40 | 42 | 40 |
| Pressure atm | 1.09 | 1.04 | 1.09 | 1 | 1 | 1.09 | 1 |
| Vapor Frac | 0 | 0.042 | 0 | 0 | 0 | 0 | 0 |
| Mole Flow kmol/hr | 1319.708 | 1319.708 | 1041.844 | 1086.487 | 869.189 | 1041.844 | 217.297 |
| Mass Flow kg/hr | 157778.244 | 157778.2 | 138286 | 51225.914 | 40980.731 | 138285.96 | 10245.183 |
| Volume Flow l/hr | 188461.269 | 1.72E+06 | 173297.9 | 62939.692 | 50351.754 | 164411.35 | 12587.939 |
| Enthalpy MMBtu/hr | −485.757 | −467.491 | −375.006 | −318.408 | −254.726 | −393.271 | −63.682 |
| Mass Flow kg/hr |  |  |  |  |  |  |  |
| I—BUOH | 18055.031 | 18055.03 | 13.829 | 41597.806 | 33278.245 | 13.829 | 8319.561 |
| WATER | 10218.361 | 10218.36 | 10170 | 9352.639 | 7482.112 | 10169.995 | 1870.528 |
| CO2 | 1397.525 | 1397.525 | 0 | 268.919 | 215.135 | 0 | 53.784 |
| OLEYLOH | 128107.326 | 128107.3 | 128102.1 | 6.549 | 5.239 | 128102.14 | 1.31 |
| Mass Frac |  |  |  |  |  |  |  |
| I—BUOH | 0.114 | 0.114 | 0 | 0.812 | 0.812 | 0 | 0.812 |
| WATER | 0.065 | 0.065 | 0.074 | 0.183 | 0.183 | 0.074 | 0.183 |
| CO2 | 0.009 | 0.009 | 0 | 0.005 | 0.005 | 0 | 0.005 |
| OLEYLOH | 0.812 | 0.812 | 0.926 | 0 | 0 | 0.926 | 0 |

|  | 16 | 17 | 18 | 19 | 21 | 42 |
|---|---|---|---|---|---|---|
| Temperature C. | 40 | 91 | 89.2 | 90.4 | 40 | 107.4 |
| Pressure atm | 1 | 0.99 | 0.99 | 0.99 | 1 | 0.99 |
| Vapor Frac | 0 | 1 | 1 | 1 | 1 | 0 |
| Mole Flow kmol/hr | 962.834 | 1457.995 | 626.468 | 2084.414 | 35.094 | 242.721 |
| Mass Flow kg/hr | 18386.07 | 48123.528 | 22992.059 | 71113.929 | 1502.003 | 17988.672 |
| Volume Flow l/hr | 18860.09 | 4.35E+07 | 1.86E+07 | 6.21E+07 | 896510.184 | 24878.997 |
| Enthalpy MMBtu/hr | −260.458 | −348.724 | −150.102 | −498.818 | −12.622 | −72.697 |
| Mass Flow kg/hr |  |  |  |  |  |  |
| I—BUOH | 1355.117 | 27715.881 | 15296.611 | 43011.493 | 58.57 | 17981.634 |
| WATER | 17007.39 | 18926.284 | 7480.313 | 26405.958 | 45.928 | 1.799 |
| CO2 | 23.559 | 1474.868 | 215.135 | 1689.982 | 1397.504 | 0 |
| OLEYLOH | 0 | 6.495 | 0.001 | 6.496 | 0 | 5.238 |
| Mass Frac |  |  |  |  |  |  |
| I—BUOH | 0.074 | 0.576 | 0.665 | 0.605 | 0.039 | 0.999609 |
| WATER | 0.925 | 0.393 | 0.325 | 0.371 | 0.031 | 0.0001 |
| CO2 | 0.001 | 0.031 | 0.009 | 0.024 | 0.93 | 0 |
| OLEYLOH | 0 | 0 | 0 | 0 | 0 | 0.000291 |

TABLE 4

Simulated BUOHCOL Column Traffic and Liquid Mass Composition Profile Outputs for Example 1.

| Stage | Temperature C. | Pressure atm | Heat duty MJ/hr | Liquid flow kg/hr | Vapor flow kg/hr | Liquid feed kg/hr | Vapor feed kg/hr | Mixed feed kg/hr | Liquid product kg/hr | Vapor product kg/hr |
|---|---|---|---|---|---|---|---|---|---|---|
| 1 | 89.1884519 | 0.986923 | 0 | 46350.5 | 22992.059 | 40980.731 | 0 | 0 | 0 | 22992.06 |
| 2 | 89.4264864 | 0.987301 | 0 | 46643.02 | 28361.831 | 0 | 0 | 0 | 0 | 0 |
| 3 | 89.5676107 | 0.987679 | 0 | 47873.3 | 28654.344 | 0 | 0 | 0 | 0 | 0 |
| 4 | 90.3004169 | 0.988057 | 0 | 52214.05 | 29884.626 | 0 | 0 | 0 | 0 | 0 |
| 5 | 93.4885685 | 0.988435 | 0 | 60929.06 | 34225.379 | 0 | 0 | 0 | 0 | 0 |
| 6 | 99.86938 | 0.988813 | 0 | 69590.2 | 42940.392 | 0 | 0 | 0 | 0 | 0 |
| 7 | 104.74387 | 0.989191 | 0 | 74355.71 | 51601.529 | 0 | 0 | 0 | 0 | 0 |
| 8 | 106.647851 | 0.98957 | 0 | 76056.62 | 56367.043 | 0 | 0 | 0 | 0 | 0 |
| 9 | 107.209088 | 0.989948 | 0 | 76543.59 | 58067.953 | 0 | 0 | 0 | 0 | 0 |
| 10 | 107.367505 | 0.990326 | 33684.93 | 17988.67 | 58554.918 | 0 | 0 | 0 | 17988.67 | 0 |

| Stage | I—BUOH | WATER | CO2 | OLEYLOH |
|---|---|---|---|---|
| 1 | 0.799755 | 0.200105 | 2.76E−05 | 0.000113 |
| 2 | 0.802908 | 0.19698 | 1.33E−07 | 0.000112 |
| 3 | 0.8174 | 0.182491 | 6.42E−10 | 0.000109 |
| 4 | 0.863212 | 0.136688 | 3.06E−12 | 0.0001 |
| 5 | 0.932947 | 0.066967 | 1.40E−14 | 8.60E−05 |
| 6 | 0.977674 | 0.022251 | 0 | 7.53E−05 |
| 7 | 0.993743 | 0.006187 | 0 | 7.05E−05 |
| 8 | 0.998312 | 0.001619 | 0 | 6.89E−05 |
| 9 | 0.999519 | 0.000412 | 0 | 6.85E−05 |
| 10 | 0.999609 | 0.0001 | 0 | 0.000291 |

TABLE 5

Simulated Solvent Column Traffic and Liquid Mass Composition Profile Outputs for Example 1.

| Stage | Temperature C. | Pressure atm | Heat duty MJ/hr | Liquid flow kg/hr | Vapor flow kg/hr | Liquid feed kg/hr | Vapor feed kg/hr |
|---|---|---|---|---|---|---|---|
| 1 | 91.0307686 | 0.986923 | 0 | 24941.054 | 48123.528 | 28630.201 | 1.0470085 |
| 2 | 94.3218869 | 0.993973 | 0 | 24461.627 | 44433.333 | 0 | 1965.643 |
| 3 | 95.1958482 | 1.001022 | 0 | 182478.04 | 41988.264 | 155812.6 | 0 |
| 4 | 95.9388599 | 1.008072 | 0 | 180648.24 | 44192.078 | 0 | 0 |
| 5 | 96.8087129 | 1.015121 | 0 | 178175.43 | 42362.271 | 0 | 0 |
| 6 | 97.8742043 | 1.022171 | 0 | 175579 | 39889.466 | 0 | 0 |
| 7 | 98.9610556 | 1.02922 | 0 | 173419.91 | 37293.031 | 0 | 0 |
| 8 | 99.8834274 | 1.036269 | 0 | 171940.32 | 35133.948 | 0 | 0 |
| 9 | 100.571281 | 1.043319 | 0 | 171058.7 | 33654.358 | 0 | 0 |
| 10 | 101.059319 | 1.050368 | 0 | 170582.18 | 32772.737 | 0 | 0 |
| 11 | 101.413868 | 1.057418 | 0 | 170344.53 | 32296.217 | 0 | 0 |
| 12 | 101.689917 | 1.064467 | 0 | 170237.67 | 32058.567 | 0 | 0 |
| 13 | 101.922677 | 1.071517 | 0 | 170199.67 | 31951.71 | 0 | 0 |
| 14 | 102.132193 | 1.078566 | 0 | 170197.14 | 31913.704 | 0 | 0 |
| 15 | 102.329237 | 1.085616 | 71639.35 | 138285.96 | 31911.176 | 0 | 0 |

| Stage | Mixed feed kg/hr | Liquid product kg/hr | Vapor product kg/hr | 1st liquid flow kg/hr | 2nd liquid flow kg/hr |
|---|---|---|---|---|---|
| 1 | 0 | 0 | 48123.5277 | 16.7814334 | 24924.2721 |
| 2 | 0 | 0 | 0 | 13.3840555 | 24448.2434 |
| 3 | 0 | 0 | 0 | 151949.232 | 30528.8109 |
| 4 | 0 | 0 | 0 | 148885.96 | 31762.2747 |
| 5 | 0 | 0 | 0 | 144817.483 | 33357.9469 |
| 6 | 0 | 0 | 0 | 140527.456 | 35051.5395 |
| 7 | 0 | 0 | 0 | 136916.435 | 36503.4771 |
| 8 | 0 | 0 | 0 | 134393.894 | 37546.429 |
| 9 | 0 | 0 | 0 | 132852.433 | 38206.2681 |
| 10 | 0 | 0 | 0 | 131988.909 | 38593.2723 |
| 11 | 0 | 0 | 0 | 131530.481 | 38814.0508 |
| 12 | 0 | 0 | 0 | 131295.6 | 38942.0744 |
| 13 | 0 | 0 | 0 | 131178.944 | 39020.7244 |
| 14 | 0 | 0 | 0 | 131123.42 | 39073.7202 |
| 15 | 0 | 138285.964 | 0 | 131056.792 | 7229.17263 |

TABLE 5-continued

Simulated Solvent Column Traffic and Liquid Mass Composition Profile Outputs for Example 1.

| Stage | I—BUOH | WATER | CO2 | OLEYLOH |
|---|---|---|---|---|
| 1 | 0.065222 | 0.934359 | 1.53E−05 | 0.000405 |
| 2 | 0.032292 | 0.967241 | 1.13E−05 | 0.000456 |
| 3 | 0.100971 | 0.196895 | 1.44E−05 | 0.702119 |
| 4 | 0.087269 | 0.203485 | 1.13E−07 | 0.709246 |
| 5 | 0.068485 | 0.212406 | 8.32E−10 | 0.719109 |
| 6 | 0.047943 | 0.222291 | 5.62E−12 | 0.729766 |
| 7 | 0.03008 | 0.231048 | 3.49E−14 | 0.738872 |
| 8 | 0.017308 | 0.237445 | 0 | 0.745247 |
| 9 | 0.009387 | 0.241515 | 0 | 0.749098 |
| 10 | 0.004899 | 0.243903 | 0 | 0.751198 |
| 11 | 0.002487 | 0.245262 | 0 | 0.752251 |
| 12 | 0.001229 | 0.246045 | 0 | 0.752726 |
| 13 | 0.000583 | 0.24652 | 0 | 0.752897 |
| 14 | 0.000254 | 0.246836 | 0 | 0.75291 |
| 15 | 0.0001 | 0.073543 | 0 | 0.926357 |

TABLE 6

Simulated Stream Outputs for Example 2.

| | 9 | 10 | 11 | 12 | 13 | 14 | 15 | 16 |
|---|---|---|---|---|---|---|---|---|
| Temperature C. | 32.2 | 73.2 | 102.3 | 40 | 40 | 42 | 40 | 40 |
| Pressure atm | 1.09 | 1.04 | 1.09 | 1 | 1 | 1.09 | 1 | 1 |
| Vapor Frac | 0 | 0.024 | 0 | 0 | 0 | 0 | 0 | 0 |
| Mole Flow kmol/hr | 754.83 | 754.83 | 497.555 | 1076.307 | 861.046 | 497.555 | 215.261 | 652.522 |
| Mass Flow kg/hr | 71097.115 | 71097.115 | 52561.076 | 50740.764 | 40592.609 | 52561.076 | 10148.152 | 12460.46 |
| Volume Flow l/hr | 85379.72 | 580448.3 | 65444.716 | 62343.744 | 9874.995 | 62103.785 | 12468.749 | 12781.732 |
| Enthalpy MMBtu/hr | −258.316 | −251.145 | −167.952 | −315.419 | −252.336 | −175.123 | −63.084 | −176.515 |
| Mass Flow kg/hr | | | | | | | | |
| I—BUOH | 17847.126 | 17847.126 | 5.256 | 41209.226 | 32967.381 | 5.256 | 8241.845 | 918.444 |
| WATER | 5850.821 | 5850.821 | 5826.851 | 9265.188 | 7412.151 | 5826.851 | 1853.038 | 11526.049 |
| CO2 | 670.198 | 670.198 | 0 | 266.347 | 213.077 | 0 | 53.269 | 15.966 |
| OLEYLOH | 46728.969 | 46728.969 | 46728.969 | 0 | 0 | 46728.969 | 0 | 0 |
| Mass Frac | | | | | | | | |
| I—BUOH | 0.251 | 0.251 | 0 | 0.812 | 0.812 | 0 | 0.812 | 0.074 |
| WATER | 0.082 | 0.082 | 0.111 | 0.183 | 0.183 | 0.111 | 0.183 | 0.925 |
| CO2 | 0.009 | 0.009 | 0 | 0.005 | 0.005 | 0 | 0.005 | 0.001 |
| OLEYLOH | 0.657 | 0.657 | 0.889 | 0 | 0 | 0.889 | 0 | 0 |

| | 17 | 18 | 19 | 21 | 42 |
|---|---|---|---|---|---|
| Temperature C. | 88.9 | 89.2 | 89 | 40 | 107.4 |
| Pressure atm | 0.99 | 0.99 | 0.99 | 1 | 0.99 |
| Vapor Frac | 1 | 1 | 1 | 1 | 0 |
| Mole Flow kmol/hr | 1125.058 | 620.611 | 1745.659 | 16.83 | 240.435 |
| Mass Flow kg/hr | 41144.652 | 22777.107 | 63921.532 | 720.312 | 17815.501 |
| Volume Flow l/hr | 3.34E+07 | 1.84E+07 | 5.18E+07 | 429936.7 | 24639.979 |
| Enthalpy MMBtu/hr | −270.515 | −148.698 | −419.211 | −6.053 | −72.01 |
| Mass Flow kg/hr | | | | | |
| I—BUOH | 27002.161 | 15153.661 | 42155.759 | 28.09 | 17813.72 |
| WATER | 13403.057 | 7410.369 | 20813.264 | 22.026 | 1.782 |
| CO2 | 739.434 | 213.077 | 952.509 | 670.196 | 0 |
| OLEYLOH | 0 | 0 | 0 | 0 | 0 |
| Mass Frac | | | | | |
| I—BUOH | 0.656 | 0.665 | 0.659 | 0.039 | 0.9999 |
| WATER | 0.326 | 0.325 | 0.326 | 0.031 | 0.0001 |
| CO2 | 0.018 | 0.009 | 0.015 | 0.93 | 0 |
| OLEYLOH | 0 | 0 | 0 | 0 | 0 |

TABLE 7

Simulated BUOHCOL Column Traffic and Liquid Mass Composition Profile Outputs for Example 2.

| Stage | Temperature C. | Pressure atm | Heat duty MJ/hr | Liquid flow kg/hr | Vapor flow kg/hr | Liquid feed kg/hr | Vapor feed kg/hr | Mixed feed kg/hr | Liquid product kg/hr | Vapor product kg/hr |
|---|---|---|---|---|---|---|---|---|---|---|
| 1 | 89.1880136 | 0.986923 | 0 | 45911.533 | 22777.11 | 40592.61 | 0 | 0 | 0 | 22777.11 |
| 2 | 89.4259234 | 0.987301 | 0 | 46201.396 | 28096.03 | 0 | 0 | 0 | 0 | 0 |
| 3 | 89.5671137 | 0.987679 | 0 | 47420.691 | 28385.89 | 0 | 0 | 0 | 0 | 0 |
| 4 | 90.3002908 | 0.988057 | 0 | 51722.168 | 29605.19 | 0 | 0 | 0 | 0 | 0 |
| 5 | 93.489625 | 0.988435 | 0 | 60356.46 | 33906.67 | 0 | 0 | 0 | 0 | 0 |
| 6 | 99.8708799 | 0.988813 | 0 | 68935.489 | 42540.96 | 0 | 0 | 0 | 0 | 0 |
| 7 | 104.744312 | 0.989191 | 0 | 73655.06 | 51119.99 | 0 | 0 | 0 | 0 | 0 |
| 8 | 106.64761 | 0.98957 | 0 | 75339.418 | 55839.56 | 0 | 0 | 0 | 0 | 0 |
| 9 | 107.208631 | 0.989948 | 0 | 75821.947 | 57523.92 | 0 | 0 | 0 | 0 | 0 |
| 10 | 107.365261 | 0.990326 | 33369.14 | 17815.501 | 58006.45 | 0 | 0 | 0 | 17815.501 | 0 |

| Stage | I—BUOH | WATER | CO2 | OLEYLOH |
|---|---|---|---|---|
| 1 | 0.799846 | 0.200127 | 2.76E−05 | 1.64E−10 |
| 2 | 0.803001 | 0.196999 | 1.33E−07 | 1.63E−10 |
| 3 | 0.817498 | 0.182502 | 6.42E−10 | 1.59E−10 |
| 4 | 0.86332 | 0.13668 | 3.06E−12 | 1.45E−10 |
| 5 | 0.933048 | 0.066952 | 1.40E−14 | 1.25E−10 |
| 6 | 0.977756 | 0.022244 | 0 | 1.09E−10 |
| 7 | 0.993815 | 0.006185 | 0 | 1.02E−10 |
| 8 | 0.998382 | 0.001618 | 0 | 9.99E−11 |
| 9 | 0.999588 | 0.000412 | 0 | 9.93E−11 |
| 10 | 0.9999 | 0.0001 | 0 | 4.22E−10 |

TABLE 8

Simulated Solvent Column Traffic and Liquid Mass Composition Profile Outputs for Example 2.

| Stage | Temperature C. | Pressure atm | Heat duty MJ/hr | Liquid flow kg/hr | Vapor flow kg/hr | Liquid feed kg/hr | Vapor feed kg/hr | Mixed feed kg/hr | Liquid product kg/hr | Vapor product kg/hr |
|---|---|---|---|---|---|---|---|---|---|---|
| 1 | 88.9422712 | 0.986923 | 0 | 26040.818 | 41144.65 | 22607.57 | 1.0376553 | 0 | 0 | 41144.65 |
| 2 | 89.1928695 | 0.993973 | 0 | 21430.278 | 44576.86 | 0 | 736.68398 | 0 | 0 | 0 |
| 3 | 92.0459809 | 1.001022 | 0 | 94496.221 | 39229.63 | 70360.43 | 0 | 0 | 0 | 0 |
| 4 | 92.3323703 | 1.008072 | 0 | 94550.968 | 41935.15 | 0 | 0 | 0 | 0 | 0 |
| 5 | 92.517813 | 1.015121 | 0 | 94561.975 | 41989.89 | 0 | 0 | 0 | 0 | 0 |
| 6 | 92.7125512 | 1.022171 | 0 | 94468.264 | 42000.9 | 0 | 0 | 0 | 0 | 0 |
| 7 | 92.9575427 | 1.02922 | 0 | 93907.442 | 41907.19 | 0 | 0 | 0 | 0 | 0 |
| 8 | 93.4298808 | 1.036269 | 0 | 91619.38 | 41346.37 | 0 | 0 | 0 | 0 | 0 |
| 9 | 94.72859 | 1.043319 | 0 | 86109.931 | 39058.3 | 0 | 0 | 0 | 0 | 0 |
| 10 | 97.4651369 | 1.050368 | 0 | 80604.9 | 33548.86 | 0 | 0 | 0 | 0 | 0 |
| 11 | 100.068667 | 1.057418 | 0 | 78122.027 | 28043.82 | 0 | 0 | 0 | 0 | 0 |
| 12 | 101.327321 | 1.064467 | 0 | 77370.843 | 25560.95 | 0 | 0 | 0 | 0 | 0 |
| 13 | 101.844136 | 1.071517 | 0 | 77178.529 | 24809.77 | 0 | 0 | 0 | 0 | 0 |
| 14 | 102.120204 | 1.078566 | 0 | 77139.76 | 24617.45 | 0 | 0 | 0 | 0 | 0 |
| 15 | 102.329061 | 1.085616 | 55155.09 | 52561.076 | 24578.68 | 0 | 0 | 0 | 52561.076 | 0 |

| Stage | 1st liquid flow kg/hr | 2nd liquid flow kg/hr | I-BUOH | WATER | CO2 | OLEYLOH |
|---|---|---|---|---|---|---|
| 1 | 12648.19 | 13392.63 | 0.441665 | 0.558303 | 3.21E−05 | 5.14E−07 |
| 2 | 4325.494 | 17104.78 | 0.2485 | 0.751206 | 1.72E−05 | 0.000277 |
| 3 | 75947.21 | 18549.01 | 0.261893 | 0.243518 | 1.50E−05 | 0.494574 |
| 4 | 75986.38 | 18564.59 | 0.262119 | 0.243593 | 9.58E−08 | 0.494288 |
| 5 | 75975.56 | 18586.42 | 0.262003 | 0.243765 | 6.16E−10 | 0.494232 |
| 6 | 75792.34 | 18675.92 | 0.26068 | 0.244596 | 3.97E−12 | 0.494724 |
| 7 | 74839.89 | 19067.55 | 0.253908 | 0.248406 | 2.55E−14 | 0.497686 |
| 8 | 71058.04 | 20561.34 | 0.226084 | 0.263772 | 0 | 0.510144 |
| 9 | 62124.16 | 23985.77 | 0.152452 | 0.304687 | 0 | 0.542861 |
| 10 | 53428.86 | 27176.04 | 0.066076 | 0.35389 | 0 | 0.580035 |
| 11 | 49511.75 | 28610.28 | 0.020756 | 0.380719 | 0 | 0.598525 |
| 12 | 48282.81 | 29088.03 | 0.005693 | 0.38995 | 0 | 0.604357 |
| 13 | 47946.52 | 29232.01 | 0.001485 | 0.392644 | 0 | 0.605871 |
| 14 | 47859.93 | 29279.83 | 0.00037 | 0.39345 | 0 | 0.60618 |
| 15 | 47806.94 | 4754.139 | 0.0001 | 0.110859 | 0 | 0.889041 |

What is claimed is:

1. A process comprising the steps:
   a) introducing a feed comprising:
      (i) a water-immiscible organic extractant,
      (ii) water,
      (iii) at least one isomer of butanol, and
      (iv) optionally a non-condensable gas
   into a first distillation column, wherein the first distillation column comprises a stripping section and optionally a rectifying section at an introduction point above the stripping section, the first distillation column having an operating temperature, $T_1$ and an operating pressure $P_1$ at a predetermined point in the stripping section, wherein $T_1$ and $P_1$ are selected to produce a first bottoms stream and a first vaporous overhead stream, the first bottoms stream comprising the water-immiscible organic extractant and water and being substantially free of the at least one isomer of butanol, and the first vaporous overhead stream comprising water, the at least one isomer of butanol, and the optional non-condensable gas;
   b) condensing the first vaporous overhead stream to produce an optional gas phase and recover a first mixed condensate, wherein the first mixed condensate comprises
      (i) a butanol phase comprising the at least one isomer of butanol and less than 30 wt % water; and
      (ii) an aqueous phase comprising water and less than 10 wt % of the at least one isomer of butanol;
   c) introducing at least a portion of the aqueous phase to the first distillation column;
   d) introducing a first portion of the butanol phase into a second distillation column having at least a stripping section;
   e) operating the second distillation column to produce a second bottoms stream comprising the at least one isomer of butanol and being substantially free of water, and a second vaporous overhead stream comprising the at least one isomer of butanol and water; and
   f) introducing at least a portion of the aqueous phase into a fermentation vessel,
   wherein the extractant is selected such that it (A) preferentially extracts the at least one isomer of butanol over water and (B) is separable from the at least one isomer of butanol by distillation.

2. The process of claim 1, optionally comprising any one of steps:
   g) introducing a second portion of the butanol phase into the first distillation column; or
   h) condensing the second vaporous overhead stream from the second distillation column to obtain a second condensate stream and introducing at least a portion of the second condensate stream into the first mixed condensate stream; or
   j) both steps g) and step h).

3. The process of claim 1, further comprising the step of adding water, steam, or a mixture thereof into the first distillation column.

4. The process of claims 1, wherein the process further comprises the step of introducing the bottoms stream from the first distillation column into a fermentation vessel.

5. The process of claim 1, wherein the process further comprises the step of separating the bottoms stream from the first distillation column to obtain a bottoms aqueous phase comprising water and a bottoms organic phase comprising the extractant, introducing at least a portion of the bottoms organic phase into a fermentation vessel, and optionally introducing at least a portion of the bottoms aqueous phase into a fermentation vessel.

6. The process of claim 1, wherein a non-condensable gas is present in the feed and the process further comprises the step of purging at least a portion of the gas phase comprising the non-condensable gas from the process.

7. The process of claim 1, wherein the non-condensable gas comprises carbon dioxide.

8. The process of claim 1, wherein the feed further comprises an organic phase obtained from an extractive fermentation.

9. The process of claim 1, wherein the concentration of the at least one isomer of butanol in the feed is from about 0.1 weight percent to about 40 weight percent, based on the weight of the feed.

10. The process of claim 1, wherein the at least one isomer of butanol is not a mixture of 1-butanol and isobutanol.

11. The process of claim 10, wherein the at least one isomer of butanol consists essentially of isobutanol.

12. The process of claim 4, wherein the extractant comprises at least one solvent selected from the group consisting of $C_7$ to $C_{22}$ fatty alcohols, $C_7$ to $C_{22}$ fatty acids, esters of $C_7$ to $C_{22}$ fatty acids, $C_7$ to $C_{22}$ fatty aldehydes, and mixtures thereof.

13. The process of claim 12, wherein the extractant is oleyl alcohol.

14. The process of claim 12, wherein the at least one isomer of butanol consists essentially of either 1-butanol or isobutanol.

* * * * *